(12) United States Patent
Ori et al.

(10) Patent No.: US 8,129,443 B2
(45) Date of Patent: Mar. 6, 2012

(54) POLYMERIZABLE COMPOSITION, CURED OBJECT OBTAINED THEREFROM, AND COMPOSITE MATERIAL

(75) Inventors: Tatsuya Ori, Moriyama (JP); Yasukazu Saimi, Moriyama (JP); Masayuki Asai, Moriyama (JP)

(73) Assignee: Sun Medical Co., Ltd., Shiga (JP)

( * ) Notice: Subject to any disclaimer, the term of this patent is extended or adjusted under 35 U.S.C. 154(b) by 720 days.

(21) Appl. No.: 10/506,090

(22) PCT Filed: Jul. 17, 2001

(86) PCT No.: PCT/JP01/06168
§ 371 (c)(1),
(2), (4) Date: Nov. 9, 2004

(87) PCT Pub. No.: WO02/14433
PCT Pub. Date: Feb. 21, 2002

(65) Prior Publication Data
US 2005/0123762 A1    Jun. 9, 2005

(30) Foreign Application Priority Data
Aug. 11, 2000    (JP) ................................. 2000-244679

(51) Int. Cl.
*A61K 6/08* (2006.01)
*A61F 6/02* (2006.01)
*C08K 3/22* (2006.01)
*B32B 5/16* (2006.01)

(52) U.S. Cl. ...... 523/113; 523/115; 523/117; 433/228.1; 106/35; 524/403; 524/431; 977/919; 428/407

(58) Field of Classification Search .................. 523/115, 523/116, 117, 118, 113; 433/228.1; 428/407; 524/403, 431; 106/35; 977/919
See application file for complete search history.

(56) References Cited

U.S. PATENT DOCUMENTS

| | | | | |
|---|---|---|---|---|
| 4,302,376 A * | 11/1981 | Walkowiak et al. | .......... | 523/117 |
| 4,306,913 A * | 12/1981 | Mabie et al. | .................. | 106/450 |
| 4,649,165 A * | 3/1987 | Kuhlmann | .................... | 523/116 |
| 5,708,051 A * | 1/1998 | Erdrich et al. | ................. | 523/116 |
| 5,883,153 A * | 3/1999 | Roberts et al. | ................. | 523/116 |
| 5,936,006 A * | 8/1999 | Rheinberger et al. | ......... | 523/116 |
| 5,962,550 A * | 10/1999 | Akahane et al. | ............... | 523/116 |
| 6,261,700 B1 * | 7/2001 | Olson et al. | ................... | 428/522 |
| 6,306,926 B1 * | 10/2001 | Bretscher et al. | ............. | 523/116 |
| 6,376,590 B2 * | 4/2002 | Kolb et al. | ..................... | 524/413 |
| 6,387,981 B1 * | 5/2002 | Zhang et al. | ................... | 523/117 |
| 6,572,693 B1 * | 6/2003 | Wu et al. | .......................... | 106/35 |
| 6,620,861 B1 * | 9/2003 | Nakatuka et al. | ............. | 523/212 |
| 6,730,156 B1 * | 5/2004 | Windisch et al. | ............... | 106/35 |
| 7,037,583 B2 * | 5/2006 | Furman et al. | ................. | 428/403 |

FOREIGN PATENT DOCUMENTS

| | | |
|---|---|---|
| JP | 60-11505 | 1/1985 |
| JP | 4-18453 | 1/1992 |
| JP | 4- 18453 | 1/1992 |
| JP | 5-209027 | 8/1993 |
| JP | 07-291817 | 11/1995 |
| JP | 8-143747 | 6/1996 |
| JP | 9-175921 | 7/1997 |
| JP | 09-175921 | 7/1997 |
| WO | WO 00/06622 | * 2/2000 |

OTHER PUBLICATIONS

Nyacol® Zirconia Colloidal Products, Nyacol Nano Technologies, Inc.; Jan. 2008.*

* cited by examiner

*Primary Examiner* — Michael Pepitone
(74) *Attorney, Agent, or Firm* — Wenderoth, Lind & Ponack, LLP

(57) ABSTRACT

There are provided a novel polymerizable composition having an X-ray contrast property and excellent transparency, a cured product thereof, and a composite material comprising powder of the cured product. More specifically, there are provided a polymerizable composition comprising (A) an inorganic oxide having an X-ray contrast property and an average particle diameter of 100 nm or smaller, (B) a surface modifier, (C) a polymerizable compound and (D) a polymerization initiator, a cured product obtained by polymerizing these components, and a composite material comprising powder of the cured product.

6 Claims, No Drawings

POLYMERIZABLE COMPOSITION, CURED OBJECT OBTAINED THEREFROM, AND COMPOSITE MATERIAL

TECHNICAL FIELD

The present invention relates to a polymerizable composition which contains an inorganic oxide having an X-ray contrast property, a cured product thereof, and a composite material comprising powder of the cured product. More specifically, it relates to a polymerizable composition in which an inorganic oxide of 100 nm or smaller is dispersed uniformly and which has not only excellent transparency and surface gloss but also an X-ray contrast property and can be used not only for industrial materials but also for dental materials, a cured product thereof, and a composite material comprising powder of the cured product.

BACKGROUND ART

In recent years, differences in various material properties have been becoming revealed, with a particle diameter of 100 nm as a boundary. For example, pigments are formed such that the particle diameters are at least a half of the wavelength of visible light for the sake of high coloring and concealing abilities. However, when the particle diameters are 100 nm or smaller, they do not show chromatic properties. Thus, the development of new toning has been expected. Meanwhile, magnetic materials show a phenomenon that multiple magnetic domain particles become single magnetic domain particles and magnetic properties change at a boundary of around 100 nm. In expectation of such a novel property, studies have been made actively on ceramic materials, colored pigments, optical materials, electroconductive materials, piezoelectric materials and the like. Meanwhile, as to the relationship between particle diameters of nano order (100 nm or smaller) and transparency, absorption, scattering and reflection must be low to improve transparency. Further, it is known that when particle diameters are equal to or smaller than ¼ of the wavelength of visible light, scattering is low and transparency is high (refer to New Development of Nano Fine Particles, Toray Research Center, Inc., pp. 3 to 6).

In general, as exemplified by titanium white powders of fine particles, a transparent cured product is still obtained by adding inorganic oxide particles powders having a refractive index different from that of a polymerizable compound by 0.1 or higher, an X-ray contrast property and a primary particle diameter of nano order in an amount of at least about 3 parts by weight to 100 parts by weight of the polymerizable compound, adding a polymerization initiator and then fully kneading them to polymerize them. The reason is as follows. That is, since the surface energy of primary particles becomes higher and the primary particles become more unstable as the inorganic oxide particles become finer, the primary particles are agglomerated firmly to lower the surface energy, thereby becoming stable. That is, when the particles are added to the polymerizable compound, the size of the agglomerated particles is already nearly equal to or larger than the wavelength of visible light, and it is extremely difficult to re-disperse most of the agglomerated primary particles, so that a transparent cured product cannot be obtained.

Meanwhile, (meth)acrylate-based materials are widely used not only as industrial materials but also as dental materials due to their properties such as excellent transparency and good surface gloss. However, a (meth)acrylate alone shows a high polymerization shrinkage ratio, and a cured product thereof shows poor mechanical strength and abrasion resistance. Thus, a number of studies have been made on a composite of the (meth)acrylate and an inorganic oxide. JP-A 60-11505 (the term "JP-A" as used herein means an "unexamined published Japanese patent application")discloses a dental composition with improved abrasion resistance which is obtained by adding a spherical inorganic oxide having a specific particle diameter to a vinyl compound and then polymerizing them. However, since the particle diameter of the inorganic oxide used in this method is 100 nm or larger, it is difficult to say that the dental composition has excellent surface gloss, and the inorganic oxide may protrude or come off by abrasion, and the resulting abraded surface is a rough resin surface. Thus, when the composition is used for dental applications, it may cause such a problem as abrasion of the opposing tooth. Further, when a large quantity of an inorganic oxide having a particle diameter of 100 nm or smaller is added to a polymerizable compound, a significant increase in the viscosity of paste occurs due to the large specific surface area of the inorganic oxide and the paste becomes unusable. On the other hand, when the quantity of the inorganic oxide is decreased, the paste becomes sticky and sticks to a spatula, so that in order to be practically used, it has a problem to be solved with respect to moldability. Meanwhile, JP-A 5-209027 discloses that a composite composition having excellent transparency and rigidity is obtained by uniformly dispersing silica in a vinyl compound by use of colloidal silica and a silane compound. According to this method, since silica of 100 nm or smaller can be dispersed uniformly, the composition has excellent transparency, and it is free of a problem of moldability caused by an increase in viscosity. Further, JP-A 7-291817 discloses use of the above composite composition as a dental composition. However, since the composition uses colloidal silica, the inorganic oxide is limited to silica, and the obtained cured product has almost no X-ray contrast property. Therefore, when it is used as dental cement, a dental filler or the like, it can hardly be detected by an X-ray, so that it is difficult to determine whether a treatment is successful and a problem may occur. Further, the publication describes nothing about a method of uniformly dispersing an inorganic oxide other than colloidal silica in the polymerizable compound. In addition, when the composition is used in industrial applications other than dental applications, hardness and abrasion resistance are improved; however, since silica is not capable of absorbing high-energy light having a shorter wavelength than that of visible light, e.g., ultraviolet light or a radiation, a cured product thereof may be degraded by yellowing or cracking when the cured product is exposed to outside.

DISCLOSURE OF THE INVENTION

The present inventors have paid attention to a colloidal solution in which fine particles having a primary particle diameter of 100 nm or smaller are dispersed uniformly in a solvent without agglomeration, so as to obtain a polymerizable composition which is imparted with an X-ray contrast property without impairing excellent transparency, surface gloss and moldability as of (meth)acrylate-based materials and a cured product thereof. That is, the present inventors have found that a polymerizable colloidal solution in which an inorganic oxide having an X-ray contrast property is dispersed in a polymerizable compound is obtained by using an aqueous colloidal solution in which the inorganic oxide having an X-ray contrast property is dispersed in water or an aqueous organic solvent as a starting material and replacing the solvent by the polymerizable compound without agglomeration (gelation) of colloidal particles and that by further developing the polymerizable colloidal solution, a novel polymerizable composition having an X-ray contrast property and excellent transparency, a cured product thereof and a composite material comprising powder of the cured product are obtained. The present inventors have achieved the present invention based on the finding.

According to the present invention, there are provided a polymerizable composition comprising (A) an inorganic oxide having an X-ray contrast property and an average particle diameter of 100 nm or smaller, (B) a surface modifier, (C) a polymerizable compound and (D) a polymerization initiator, a cured product obtained by polymerizing these components, and a composite material comprising powder of the cured product.

A characteristic of the present invention is that not only uniform dispersion of an inorganic oxide having a primary particle diameter of an order of nanometer such as 100 nm or smaller in a polymerizable compound which has been difficult to achieve but also impartation of an X-ray contrast property to a cured product obtained from the polymerizable composition have become possible by use of a colloidal solution in which an inorganic oxide having an X-ray contrast property is uniformly dispersed in water or an aqueous organic solvent, e.g., an alcohol such as methanol or ethanol or acetone as a starting material. Another characteristic of the present invention is that since the inorganic oxide has an average particle diameter of 100 nm or smaller, there can be provided a polymerizable composition having better abrasion resistance and mechanical properties while retaining excellent transparency and surface gloss as of (meth)acrylate-based materials, a cured product thereof, and powder of the cured product. Further, these cured product and powder also have an advantage that color matching of dental filler, dental cement or the like is easily done due to their excellent transparency.

Hereinafter, the present invention will be further described. Thereby, the characteristics of the present invention will become more apparent.

As the inorganic oxide (A) having an X-ray contrast property and an average particle diameter of 100 nm or smaller and used in the present invention, a variety of commercial products and synthetic products can be used. The inorganic oxide may be any inorganic oxide having an X-ray contrast property. Specific examples of the inorganic oxide include inorganic oxides of aluminum, titanium, yttrium, zirconium, niobium, lanthanide, antimony, barium, hafnium or strontium, inorganic oxides containing two or more elements at the same time such as barium titanate, and inorganic oxides resulting from mixing two or more inorganic oxides. Of these, the elements of the groups 2A to 7B excluding silicon which constitutes silica are preferred, and inorganic oxides of titanium and zirconium are particularly preferably used due to such a reason that they are not so harmful to living bodies. Further, together with these inorganic oxides, silica having almost no X-ray contrast property can be used as long as the properties of the present invention are not impaired. Silica may also be contained and used in the inorganic oxide as a composite such as a silica/zirconia composite. The average particle diameter of the inorganic oxide is generally 1 to 100 nm. It is preferably 1 to 60 nm, more preferably 1 to 30 nm, in view of transparency. The average particle diameter of the inorganic oxide is determined by a transmission electron microscope.

The inorganic oxide having an average particle diameter of 100 nm or smaller and used in the present invention can be generally acquired as an aqueous colloidal solution of water, an aqueous organic solvent or a mixed solvent of water and an aqueous organic solvent. As the solvent of the aqueous colloidal solution of the inorganic oxide, an aqueous organic solvent, e.g., an alcohol having 1 to 5 carbon atoms such as methanol, ethanol and isopropyl alcohol, cellosolves and dimethyl acetamide, water or the like is used. Preferably, an alcohol which can be uniformly mixed with water, cellosolve and water are used alone or in admixture. Further, as long as colloidal particles are not agglomerated, the aqueous organic solvent and water may be mixed together in a given ratio and used. Although the pH of the solution of the inorganic oxide (A) is not particularly limited, the solution is preferably neutral or acidic to use the following surface modifier (B), and the pH is particularly preferably 3 to 7.

In the aqueous colloidal solution of the inorganic oxide (A), a colloid stabilizer (E) is generally contained in an amount of 0.1 to 70 wt % based on 100 parts by weight of (A). Illustrative examples of the colloid stabilizer (E) include acidic compounds such as hydrochloric acid, nitric acid, oxalic acid and acetic acid and alkaline compounds such as ammonia.

The surface modifier (B) used in the present invention may be any surface modifier which can modify the surface of the inorganic oxide (A). An alkoxysilane compound is preferably used. In particular, an alkoxysilane compound represented by the following formula (I):

wherein $R^1$ and $R^2$ each independently represent a substituent with 1 to 20 carbon atoms which may have an ether bond, an ester bond, an epoxy bond or a carbon-carbon double bond and which may also have a nitrogen atom, a sulfur atom or a phosphorus atom, $R^3$ represents a hydrogen atom or a substituent with 1 to 20 carbon atoms which may have an ether bond, an ester bond or a carbon-carbon double bond and which may also have a nitrogen atom, a sulfur atom or a phosphorus atom, a and b represent an integer of 0 to 3, and c satisfies c=4−a−b and represents an integer of 1 to 4, is preferably used. Alkoxysilane compounds represented by the following formulae (I-A) to (I-F):

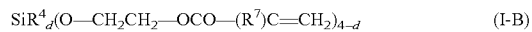

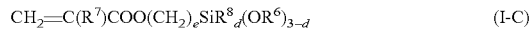

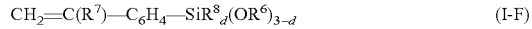

wherein $R^4$ and $R^5$ each independently represent a substituent with 1 to 20 carbon atoms which may have an ether bond, an ester bond, an epoxy bond or a carbon-carbon double bond and which may also have a nitrogen atom, a sulfur atom or a phosphorus atom, $R^6$ represents a hydrogen atom or a hydrocarbon residue having 1 to 20 carbon atoms, $R^7$ represents a hydrogen atom or a methyl group, $R^8$ represents an alkyl group having 1 to 3 carbon atoms or a phenyl group, a and b represent an integer of 0 to 3, c satisfies c=4−a−b and represents an integer of 1 to 4, d represents an integer of 0 to 2, and e represents an integer of 1 to 6, are particularly preferably used.

Illustrative examples of the silane compound represented by the above formula (I-A) include tetramethoxysilane, tetraethoxysilane, tetrapropoxysilane, tetrabutoxysilane, methyl triethoxysilane, ethyl trimethoxysilane, ethyl triethoxysilane, phenyl trimethoxysilane, phenyl triethoxysilane, dimethyl dimethoxysilane, diphenyl dimethoxysilane, methylethyl diethoxysilane, methylphenyl dimethoxysilane, trimethylmethoxysilane, trimethylethoxysilane, methoxyethyl triethoxysilane, trimethoxyhexylsilane, trimethoxyoctylsilane, acetoxyethyl triethoxysilane, tetraacetoxysilane, methyl triacetoxysilane, tetrakis(2-methoxyethoxy)silane, γ-glycidoxypropyl trimethoxysilane, γ-glycidoxypropyl triethoxysilane, γ-glycidoxypropylmethyl dimethoxysilane, γ-glycidoxypropylmethyl diethoxysilane, β-(3,4-epoxycyclohexyl)ethyl trimethoxysilane and β-(3,4-epoxycyclohexyl)ethyl triethoxysilane.

Illustrative examples of the silane compound represented by the above formula (I-B) include tetrakis(acryloxyethoxy)silane, tetrakis(methacryloxyethoxy)silane and methyl tris(methacryloxyethoxy)silane.

Illustrative examples of the silane compound represented by the above formula (I-C) include β-(meth)acryloxyethyl dimethoxymethylsilane, γ-(meth)acryloxypropyl methoxydimethylsilane, γ-(meth)acryloxypropyl trimethoxysilane, β-(meth)acryloxyethyl diethoxymethylsilane, γ-(meth)acryloxypropyl ethoxydimethylsilane, γ-(meth)acryloxypropyl dimethylethoxysilane, γ-(meth)acryloxypropyl methyldiethoxysilane, and γ-(meth)acryloxypropyl triethyloxysilane.

Illustrative examples of the silane compound represented by the above formula (I-D) include vinyl methyl dimethoxysilane, vinyl trimethoxysilane and vinyl triethoxysilane.

Illustrative examples of the silane compound represented by the above formula (I-E) include γ-mercaptopropyl dimethoxymethylsilane and γ-mercaptopropyl trimethoxysilane.

Illustrative examples of the silane compound represented by the above formula (I-F) include p-vinyl phenylmethyl dimethoxysilane and p-vinyl phenyl trimethoxysilane.

As compounds containing hetero atoms, generally used silane coupling agents such as N-β(N-vinylbenzylaminoethyl)-γ-aminopropyl trimethoxysilane hydrochloride, γ-mercaptopropyl trimethoxysilane and octadecyl dimethyl[3-(trimethoxysilyl)propyl]ammonium chloride can also be used without limitations.

Of the compounds represented by the above formula (I), γ-(meth)acryloxypropyl dimethyl methoxysilane, γ-(meth)acryloxypropyl methyl dimethoxysilane, γ-(meth)acryloxypropyl trimethoxysilane, γ-(meth)acryloxypropyl dimethyl ethoxysilane, γ-(meth)acryloxypropyl methyl diethoxysilane and γ-(meth)acryloxypropyl triethoxysilane are particularly preferably used.

Further, titanium-based, zirconia-based, aluminum-based and zircoaluminate-based surface modifiers different from the above surface modifiers can also be used without any problems. Further, the silane coupling agents represented by the above formula (I) and the surface modifiers other than these silane coupling agents can be used together without any problems as long as the properties of the composite material of the present invention are not impaired.

Next, the amount of the surface modifier (B) to be added to the aqueous colloidal solution containing the inorganic oxide (A) and a method of adding the surface modifier (B) to the aqueous colloidal solution will be described. When the amount of the surface modifier (B) is too small, the inorganic oxide is not dispersed uniformly when the solvent is replaced by the polymerizable compound, so that a polymerizable composition having excellent transparency and a cured product thereof may not be obtained disadvantageously. Accordingly, the preferred amount of the surface modifier (B) is preferably 10 to 500 parts by weight, more preferably 10 to 350 parts by weight, particularly preferably 10 to 250 parts by weight, based on 100 parts by weight of the inorganic oxide (A). When a hydrolyzed or partially hydrolyzed compound or a compound resulting from condensation of two or more molecules is to be added, it is preferably added in the above amount. Further, when the above alkoxysilane compound is used as the surface modifier (B), a method of adding the alkoxysilane compound is not particularly limited, and a method of directly adding a solution of the alkoxysilane compound as the surface modifier (B) in an aqueous organic solvent to the aqueous colloidal solution containing the inorganic oxide (A) or a method of adding a hydrolysate of the surface modifier (B) can be used. When a hydrolysate of the surface modifier (B) is to be added, there can be employed a method using a solution prepared by adding water or a uniform solution of alcohol and acidic water in an amount of at least 0.5 moles per mole of the alkoxysilane compound and then treating the mixture at room temperature to a reflux temperature for several minutes to several tens of hours.

The solid concentration of the aqueous colloidal solution containing the inorganic oxide (A) is preferably 1 to 50 wt %, more preferably 1 to 30 wt %. When the solid concentration is lower than 1 wt %, the solution is so dilute that when the organic solvent or water which is a dispersion medium of the colloidal solution is replaced by the polymerizable compound, the amount removed of the solvent becomes large or the amount added of the polymerizable compound (C) becomes so low that a decrease in the productivity of the polymerizable composition may occur. Meanwhile, when the solid concentration is higher than 50 wt %, the colloidal solution becomes unstable and is liable to gel disadvantageously.

In one example of preferable methods for preparing the polymerizable composition, the aqueous colloidal solution of the inorganic oxide is prepared, with or without being mixed with an aqueous solvent which does not cause the colloidal solution to gel such as methanol, ethanol or isopropyl alcohol, such that the solid concentration of the colloidal solution becomes 1 to 30 wt %. After the alkoxysilane compound is added to this solution, the resulting solution is stirred at room temperature to a reflux temperature for several minutes to several tens of hours, and the polymerizable compound is then added. Alternatively, it is also possible that the alkoxysilane compound and the aqueous solvent such as methanol are mixed uniformly first and the aqueous colloidal solution of the inorganic oxide is added thereto and stirred to achieve a desired solid concentration. Alternatively, a compound resulting from hydrolyzation or partial hydrolyzation of the alkoxysilane compound or condensation of two or more molecules of the compound may be added to the colloidal solution and stirred as described above. As long as the transparency of the colloidal solution is not degraded and gelation of the colloidal solution is not induced, the polymerizable compound to replace the solvent may be added to the colloidal solution immediately after addition of the alkoxysilane compound or the alkoxysilane compound and the polymerizable compound may be added simultaneously and stirred. Further, when the colloidal solution containing the inorganic oxide (A) is not an acidic solution, an acidic compound may be added to the colloidal solution in order to adjust the rate of hydrolysis of the alkoxysilane compound and promote the affinity of the alkoxysilane compound for the inorganic oxide, as long as colloidal particles do not gel. As the acidic compound, an inorganic acid or an organic acid can be used. Illustrative examples of the inorganic acid include halogenated hydroacids such as hydrogen fluoride, hydrogen bromide and hydrochloric acid, and mineral acids such as nitric acid, sulfuric acid and phosphoric acid. Illustrative examples of the organic acid include formic acid, acetic acid, oxalic acid, acrylic acid and methacrylic acid. Of these, hydrochloric acid and acetic acid can be preferably used. Further, the colloidal solution containing the inorganic oxide (A) is preferably not an alkaline solution because the silane coupling agent may gel alone.

A method of replacing the alcohol or water which is a dispersion medium of the colloidal solution containing the above alkoxysilane compound with the polymerizable compound is not particularly limited, and a known method can be used. For example, it is possible that after a given amount of the polymerizable compound is added directly to the colloidal solution and stirred until the solution becomes uniform, the solution is heated at normal pressure or heated under reduced pressure by a rotary evaporator or the like to remove the alcohol or water, or the polymerizable compound is gradually added as the alcohol or water is removed by reflux at normal pressure. To be more specific about the method of removing the dispersion medium and the amount removed of the dispersion medium, it is not removed all at once by a rotary evaporator or the like, but it is preferable that about 60 parts by weight (about 60 wt % of the solvent) based on 100 parts by weight of the solvent to be removed be removed first, about 60 parts by weight of solvent azeotropic with water such as isopropyl alcohol be then added, and the solution be heated again under reduced pressure to remove the solvent. Thereby, the inorganic oxide can be dispersed uniformly in the polymerizable compound, and the target polymerizable composition is obtained. In the polymerizable composition, the colloid stabilizer (E) is preferably contained in an amount of 0.1 to 150 parts by weight, more preferably 0.1 to 100 parts by weight, particularly preferably 0.1 to 80 parts by weight, based on 100 parts by weight of (A). To remove an acidic compound such as the colloid stabilizer (E) and impurities such as halogen from the polymerizable composition, a known method can be used. For example, the polymerizable composition may be rinsed with water or an alkaline solution, an acidic compound absorbent (such as KYOWORD of Kyowa Chemical Industry Co., Ltd.) comprising molecular sieves, zeolite, Al, Mg, Si or the like may be added to absorb or adsorb the acidic compound, the acidic compound may be removed from the polymerizable composition or a solution obtained by diluting the polymerizable composition with an organic solvent by a dialysis membrane or an ultrafiltration method, or a cured product obtained by polymerizing the polymerizable composition or powder obtained by milling the cured product may be rinsed with a solvent such as water or an aqueous organic solvent in which the acidic compound is soluble or may be neutralized with an alkaline aqueous solution to remove the acidic compound. Further, the acidic compound may be removed by use of zeolite, molecular sieves, an acidic compound absorbent, a dialysis membrane or an ultrafiltration membrane in accordance with an ordinary method. When a cured product obtained by polymerizing the polymerizable composition or powder of the cured product is used in a composite material, the colloid stabilizer (E) is preferably removed completely.

The type of the polymerizable compound (C) used in the present invention is not particularly limited, and a variety of conventionally known polymerizable compounds can be used. Preferably, the following polymerizable monofunctional, bifunctional and polyfunctional (meth)acrylates, urethane compounds and polyester di(meth)acrylate compounds can be used and are selected as appropriate according to application purposes. Examples of the polymerizable compounds are as follows.

(i) Monofunctional Polymerizable Compounds

Illustrative examples of monofunctional polymerizable compounds include (meth)acrylates such as methyl (meth)acrylate, ethyl (meth)acrylate, propyl (meth)acrylate, isopropyl (meth)acrylate, butyl (meth)acrylate, pentyl (meth)acrylate, isopentyl (meth)acrylate, glycidyl (meth)acrylate, tetrafurfuryl (meth)acrylate, 2-hydroxyethyl (meth)acrylate, 2-hydroxypropyl (meth)acrylate, 3-chloro-2-hydroxypropyl (meth)acrylate, ethylene glycol mono(meth)acrylate, diethylene glycol mono(meth)acrylate, triethylene glycol mono(meth)acrylate, polyethylene glycol mono(meth)acrylate, methoxy diethylene glycol mono(meth)acrylate, methoxy tetraethylene glycol (meth)acrylate, methoxy polyethylene glycol (meth)acrylate, β-(meth)acryloxyethyl hydrogen phthalate, β-(meth)acryloxyethyl hydrogen succinate, nonylphenoxyethyl (meth)acrylate, phenoxyethyl (meth)acrylate, phenoxy diethylene (meth)acrylate, N-(2-hydroxy-3-(meth)acryloyloxypropyl)-N-phenyl glycine, N-(meth)acryloyl glycine and 4-(meth)acryloyloxyethyl trimellitic anhydride; vinyl esters such as vinyl acetate and vinyl propionate; vinyl ethers such as methyl vinyl ether, ethyl vinyl ether, isobutyl vinyl ether and (meth)acryl aldehyde ethyl acetal; alkenyl benzenes such as styrene, vinyl toluene, α-methyl styrene and chlorostyrene; vinyl cyanides such as acrylonitrile and methacrylonitrile; (meth)acryl aldehydes such as (meth) acryl aldehyde and 3-cyano (meth) acryl aldehyde; (meth)acrylic amides such as (meth)acrylamide, N-succin (meth)acrylamide and N,N-dimethyl (meth)acrylamide; (meth)acrylic acids such as (meth)acrylic acid, vinyl acetic acid and crotonic acid or metal salts thereof; phosphate-group-containing polymerizable compounds such as acid phosphoethyl (meth)acrylate, acid phosphopropyl (meth)acrylate and 2-(meth)acryloyloxyethylphenyl phosphoric acid or metal salts thereof; and sulfonic-group-containing polymerizable compounds such as allyl sulfonic acid, methallyl sulfonic acid, styrene sulfonic acid and t-butyl acrylamide sulfonic acid or metal salts thereof. Methyl methacrylate and ethyl methacrylate are particularly preferred.

(ii) Bifunctional Polymerizable Compounds

The bifunctional polymerizable compound is a compound represented by the following general formula (II):

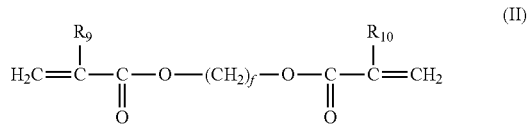

wherein f is an integer of 1 to 30, and $R^9$ and $R^{10}$ each independently represent H or an alkyl group having 1 to 5 carbon atoms. Illustrative examples of the compound include di(meth)acrylates such as propanediol, butanediol, hexanediol, octanediol, nonanediol, decanediol and eicosanediol; ethylene glycol di(meth)acrylate, diethylene glycol di(meth)acrylate, triethylene glycol di(meth)acrylate, propylene glycol di(meth)acrylate, tetraethylene glycol di(meth)acrylate, polyethylene glycol di(meth)acrylate, 1,3-butylene glycol di(meth)acrylate, neopentyl glycol di(meth)acrylate; urethane-based polymerizable compounds derived from adducts of hydroxyl-group-containing vinyl compounds such as 2-hydroxyethyl (meth)acrylate, 2-hydroxypropyl (meth)acrylate and 3-chloro-2-hydroxypropyl (meth)acrylate and diisocyanate compounds such as hexamethylene diisocyanate, trimethylhexamethylene diisocyanate, diisocyanate methylcyclohexane, isophorone diisocyanate and methyl bis(4-cyclohexylisocyanate); (meth)acrylate-based polymerizable compounds having an aromatic ring and an urethane bond and derived from adducts of hydroxyl-group-containing vinyl compounds such as 2-hydroxyethyl (meth)acrylate, 2-hydroxypropyl (meth)acrylate and 3-chloro-2-hydroxypropyl (meth)acrylate and aromatic-containing diisocyanate compounds such as diisocyanate methylbenzene and 4,4'-diphenylmethane diisocyanate; and (meth)acrylate-based polymerizable compounds having an aromatic ring and an ether bond such as 2,2-bis((meth)acryloxyphenyl)propane, 2,2-bis[4-(3-(meth)acryloxy)-2-hydroxypropoxyphenyl]propane, 2,2-bis(4-(meth)acryloxyethoxyphenyl)propane, 2,2-bis(4-(meth)acryloxydiethoxyphenyl)propane, 2,2-bis(4-(meth)acryloxytetraethoxyphenyl)propane, 2,2-bis(4-(meth)acryloxypentaethoxyphenyl)propane, 2,2-bis(4-(meth)acryloxypolyethoxyphenyl)propane, 2,2-bis(4-(meth)acryloxydipropoxyphenyl)propane, 2(4-(meth)acryloxyethoxyphenyl)-2(4-(meth)acryloxyphenyl)propane, 2(4-(meth)acryloxydiethoxyphenyl)-2(4-(meth)acryloxytriethoxyphenyl)propane, 2(4-(meth)acryloxydiethoxyphenyl)-2(4-(meth) acryloxytriethoxyphenyl)propane, 2(4-(meth)acryloxydipropoxyphenyl)-2(4-(meth)acryloxytriethoxyphenyl)propane, and 2,2-bis(4-(meth)acryloxyisopropoxyphenyl)propane. Of these, triethylene glycol dimethacrylate and di (methacryloxy ethyl)trimethylhexamethylene diurethane are particularly preferably used.

(iii) Polymerizable Compounds Having Three or More Functional Groups

A (meth)acrylate compound having three or more ethylenic unsaturated groups in a molecule may be a compound represented by the following formula (III):

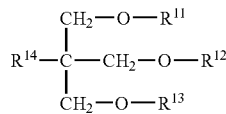
(III)

wherein $R^{11}$, $R^{12}$ and $R^{13}$ are each independently a group represented by the following formula:

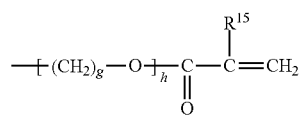

(wherein g is 1 to 10, h is 0 to 2, and $R^{15}$ is H or an alkyl group having 1 to 5 carbon atoms),
and $R^{14}$ is H, an alkyl group having 1 to 5 carbon atoms or a hydroxyalkyl group having 1 to 5 carbon atoms, or
$R^{11}$, $R^{12}$, $R^{13}$ and $R^{14}$ are each independently a group represented by the following formula:

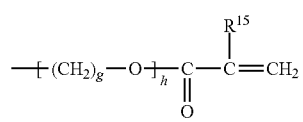

(wherein g is 1 to 10, h is 0 to 2, and $R^{15}$ is H or an alkyl group having 1 to 5 carbon atoms.)

Two or more compounds represented by the formula (III) may be used together.

Illustrative examples of the compound represented by the formula (III) include trimethylolmethane tri(meth)acrylate, trimethylolethane tri(meth)acrylate, trimethylolpropane tri(meth)acrylate, trimethylolbutane tri(meth)acrylate, tri(methyleneoxyl)methylolmethane tri(meth)acrylate, tri(ethyleneoxyl)methylolmethane tri(meth)acrylate, tri(propyleneoxyl)methylolmethane tri(meth)acrylate, tri(diethyleneoxyl)methylolmethane tri(meth)acrylate, tri(dipropyleneoxyl)methylolmethane tri(meth)acrylate, pentaerythritol tri(meth)acrylate, and pentaerythritol tetra (meth)acrylate. Of these, trimethylolpropane tri(meth)acrylate is preferably used.

Further, the (meth)acrylate compound having three or more ethylenic unsaturated groups in a molecule may be a compound represented by the following formula (IV):

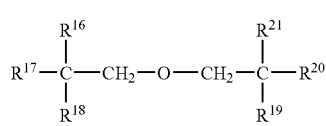
(IV)

wherein $R^{16}$, $R^{17}$, $R^{18}$, $R^{19}$, $R^{20}$ and $R^{21}$ are each independently a group represented by the following formula:

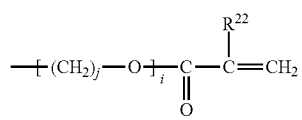

(wherein i is 1 to 10, j is 0 to 2, and $R^{22}$ is H or an alkyl group having 1 to 5 carbon atoms), or $R^{16}$, $R^{17}$, $R^{20}$ and $R^{21}$ are each independently a group represented by the following formula:

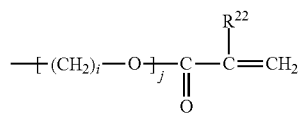

(wherein i is 1 to 10, j is 0 to 2, and $R^{22}$ is H or an alkyl group having 1 to 5 carbon atoms), and $R^{18}$ and $R^{19}$ each independently represent H, an alkyl group having 1 to 5 carbon atoms or a hydroxyalkyl group having 1 to 5 carbon atoms.

Illustrative examples of the compound represented by the formula (IV) include dipentaerythritol penta(meth)acrylate, pentaerythritol hexa(meth)acrylate, dipentaerythritol hexa (meth)acrylate, and ditrimethylolpropane tetra(meth)acrylate. Of these, dipentaerythritol hexa(meth)acrylate and ditrimethylolpropane tetra(meth)acrylate are preferably used, and ditrimethylolpropane tetra(meth)acrylate is more preferred.

Further, illustrative examples of a polyester di(meth)acrylate compound having an ethylenic unsaturated group in a molecule include a compound represented by the following formula (V):

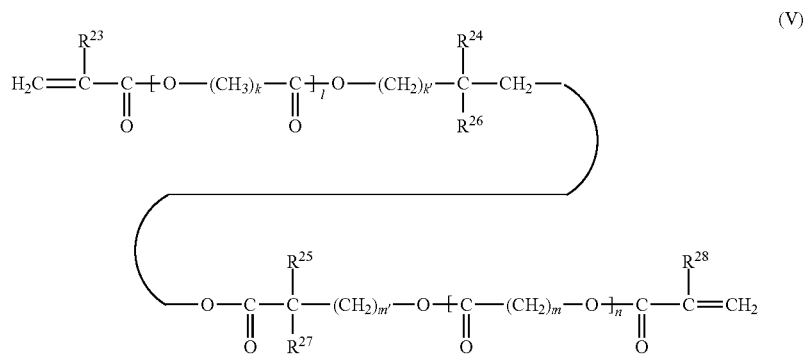

(wherein k, k', m and m' are 1 to 10, l and n are 0 to 7 and satisfy 1+n≧1, $R^{23}$ and $R^{28}$ are each independently H or an alkyl group having 1 to 5 carbon atoms, and $R^{24}$, $R^{25}$, $R^{26}$ and $R^{27}$ each independently represent H or an alkyl group having 1 to 5 carbon atoms), a compound represented by the following formula (VI):

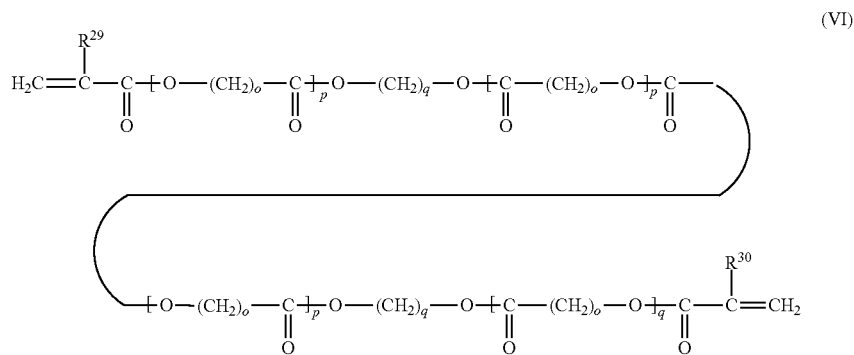

(wherein o is 1 to 10, p is 0 to 7, q is 1 to 10, $R^{29}$ and $R^{30}$ are each independently H or an alkyl group having 1 to 5 carbon atoms), and a compound represented by the following formula (VII):

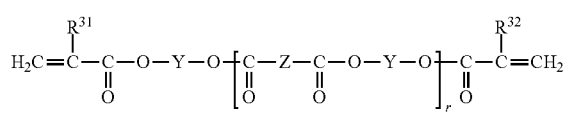

(wherein Y is a group represented by $-(CH_2)_n-$, $-CH_2CH(CH_3)-$, $-CH_2C(CH_3)_2CH_2-$, $-CH_2C_6H_{10}CH_2-$, $-CH_2CH_2(OCH_2CH_2)_t-$,

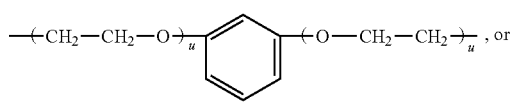

-continued

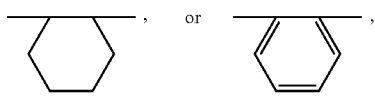

s is 2 to 6, t is 1 to 15, u is 1 to 10, v is 1 to 5, $R^{31}$ and $R^{32}$ are each independently H or an alkyl group having 1 to 5 carbon atoms, Z is a group represented by $-CH_2CH_2-$,

[cyclohexyl] , or [phenyl] , and r is an integer of 1 to 3.)

The above polyester di(meth)acrylates have a plurality of ester bonds and (meth)acryloyl groups in a molecule and generally include all compounds obtained by a reaction between a polybasic acid anhydride and a (meth)acrylate having a hydroxyl group or a dehydration reaction in between a polybasic acid, a polyhydric alcohol and (meth)acrylic acid.

Two or more of the compounds represented by the above formulae (V), (VI) and (VII) may be used together. Further, a polyester di(meth)acrylate represented by the above formula (V) in which k=m=5 and 1+n=2 or k=m=5 and 1+n=4 is preferably used, and a polyester di(meth)acrylate represented by the following formula (VIII) which is the above formula (V) in which k=m=5, k'=m'=1 and 1+n=2 or k=m=5, k'=m'=1 and 1+n=4 and $R^{24}$, $R^{25}$, $R^{26}$ and $R^{27}$ are $CH_3$ is more preferably used.

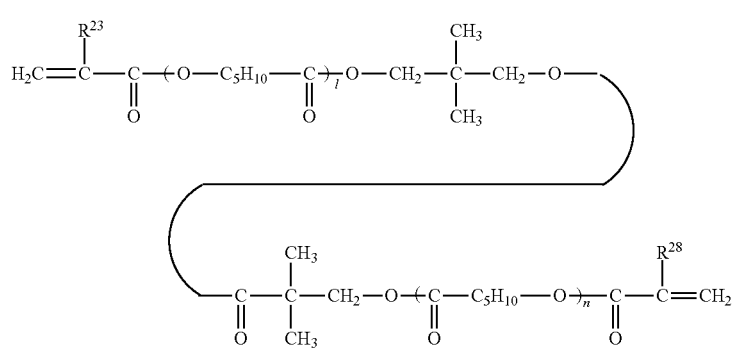

(VIII)

Polymerizable compounds having two or more functional groups include compounds having a methacrylate group and an acrylate group in a molecule, such as triethylene glycol acrylate methacrylate, trimethylolpropane monoacrylate dimethacrylate and pentaerythtitol diacrylate dimethacrylate.

A monofunctional compound is preferably mixed with a polymerizable compound having two or more functional groups before use because strength and the like may deteriorate when the monofunctional compound is used alone. The content of the polymerizable compound (C) in the polymerizable composition of the present invention is preferably 10 to 1,000 parts by weight, more preferably 10 to 800 parts by weight, particularly preferably 10 to 600 parts by weight, based on 100 parts by weight of the inorganic oxide (A), from the viewpoints of an X-ray contrast property and operability to be imparted.

As the polymerization initiator (D) used in the present invention, known polymerization initiators such as a heat polymerization or photopolymerization initiator and a redox-based initiator can be used without limitations. As the heat polymerization initiator, an organic peroxide, a diazo-based compound or the like can be preferably used. When it is desired that polymerization be carried out efficiently in a short time, a compound whose decomposition half life at 80° C. is 10 hours or less is preferred. Illustrative examples of the organic peroxide include diacyl peroxides such as acetyl peroxide, isobutyl peroxide, decanoyl peroxide, benzoyl peroxide and succinic peroxide; peroxydicarbonates such as diisopropyl peroxydicarbonate, di-2-ethylhexyl peroxydicarbonate and diallyl peroxydicarbonate; peroxyesters such as t-butyl peroxyisobutyrate, t-butyl neodecanate and cumene peroxyneodecanate; and sulfonyl peroxides such as acetyl cyclohexyl sulfonyl peroxide. Illustrative examples of the diazo-based compounds include 2,2'-azobisisobutylonitrile, 4,4'-azobis(4-cyanovaleric acid), 2,2'-azobis(4-methoxy-2,4-dimethoxyvaleronitrile) and 2,2'-azobis(2-cyclopropylpropionitrile). Benzoyl peroxide and 2,2'-azobisisobutylonitrile are particularly preferred. Further, as the redox initiator, a reducing agent such as an amine can be used together with the heat polymerization initiator. Further, as the photopolymerization initiator, a photosensitizer or a combination of a photosensitizer and a photopolymerization accelerator can be used. Illustrative examples of the photosensitizer include known compounds which are excited and initiate polymerization by irradiation of visible light or ultraviolet light, such as benzyl, an α-diketone compound, camphorquinone, α-naphthyl, p,p'-dimethoxybenzyl, pentadione, 1,4-phenanthrenequinone, naphthoquinone, and an acyl phosphine oxide derivative such as diphenyl trimethyl benzoyl phosphine oxide. These may be used alone or in combination of two or more. Camphorquinone and diphenyl trimethyl benzoyl phosphine oxide are particularly preferably used.

Illustrative examples of the photopolymerization accelerator include organic peroxides such as benzoyl oxide, acyl phosphine oxides or derivatives thereof, tertiary amines such as N,N-dimethyl aniline, N,N-diethyl aniline, N,N-dibenzyl aniline, N,N-dimethyl-p-toluidine, p-N,N-dimethylaminobenzoic acid, p-N,N-diethylaminobenzoic acid, ethyl p-N,N-dimethylaminobenzoate, ethyl p-N,N-diethylaminobenzoate, methyl p-N,N-dimethylaminobenzoate, methyl p-N,N-diethylaminobenzoate, p-N,N-dimethylaminobenzaldehyde, 2-n-butoxyethyl p-N,N-dimethylaminobenzoate, 2-n-butoxyethyl p-N,N-diethylaminobenzoate, p-N,N-dimethylaminobenzonitrile, p-N,N-diethylaminobenzonitrile, p-N,N-dihydroxyethyl aniline, p-dimethylaminophenethyl alcohol, N,N-dimethylaminoethyl methacrylate, triethylamine, tributylamine, tripropylamine and N-ethyl ethanolamine, combinations of citric acid, malic acid or 2-hydroxypropanoic acid and the above tertiary amines, barbituric acids such as 5-butylaminobarbituric acid and 1-benzyl-5-phenyl barbituric acid, and organic peroxides such as benzoyl peroxide and di-t-butyl peroxide. They may be used alone or in admixture of two or more. Tertiary aromatic amines in which a nitrogen atom is directly bonded to an aromatic or aliphatic tertiary amines having a polymerizable group, such as ethyl p-N,N-dimethylaminobenzoate, 2-n-butoxyethyl p-N,N-dimethylaminobenzoate and N,N-dimethylaminoethyl methacrylate, acyl phosphine oxides or derivatives thereof are particularly preferably used. To end curing quickly, a combination of a photosensitizer and a photopolymerization accelerator is preferred. For example, a combination of camphorquinone and a tertiary aromatic amine ester compound in which a nitrogen atom is directly bonded to an aromatic, such as ethyl p-N,N-dimethylaminobenzoate or 2-n-butoxyethyl p-N,N-dimethylaminobenzoate or an acyl phosphine oxide is preferably used. The photopolymerization accelerator is preferably used in an amount of 1 to 100 parts by weight, based on 100 parts by weight of the polymerization initiator. The amount of the polymerization initiator (D) in the present invention is preferably 0.01 to 5 parts by weight, more preferably 0.01 to 1 part by weight, based on 100 parts by weight of the total of the components (A), (B) and (C).

As for addition of the polymerization initiator to the polymerizable composition, it may be added by use of a kneader after preparation of a polymerizable colloidal solution, or a solution obtained by dissolving the polymerization initiator in an organic solvent may be added to and dispersed in the polymerizable colloidal solution during the preparation step of the polymerizable colloidal solution as long as agglomeration of inorganic oxides does not occur and the transparency of the colloidal solution is not affected.

A polymerization method for obtaining a cured product of the polymerizable composition is not particularly limited, and a known polymerization method can be employed. Further, to obtain powder (F) of the cured product of the polymerizable composition, a method comprising charging the polymerizable composition into a mold and heat-setting the composition by a heating compression molding machine under a pressure of 0.1 to 20 MPa at 60 to 200° C. for several minutes to several hours can be preferably used since it facilitates the operation of polymerization. This cured product is then milled by use of a dry mill such as a ball mill or a jet mill or a wet mill such as an apex mill, thereby giving the powder. If necessary, the powder may be classified to desired particle diameters by a sieve or the like before use. The average particle diameter of the powder of the cured product is preferably 1 to 100 µm, more preferably 1 to 50 µm, particularly preferably 1 to 35 µm. Further, a peroxide is produced during milling of the cured product, and when the resulting powder including the peroxide is added to the polymerizable compound as it is, the storage stability of paste may become significantly poor. Thus, the powder is preferably used after treated with a sodium sulfite aqueous solution, rinsed with water and dried or after heat-treated in a nitrogen atmosphere under an air current at 60 to 180° C., preferably 80 to 150° C., for several minutes to several tens of hours, preferably several hours to several tens of hours, so as to reduce the produced peroxide.

Thus, the cured product is obtained by polymerizing the polymerizable composition containing the polymerization initiator. To improve the stability of the polymerizable composition, a known polymerization inhibitor such as hydroquinone, 4-methoxyphenol, 2,6-di-t-butyl-p-cresol or hindered amine may be added. The amount of the polymerization inhibitor is not particularly limited but preferably ranges from 50 to 5,000 ppm based on the polymerizable compound.

As for the transparency of the cured product of the polymerizable composition, the cured product should have transparency of such a degree that does not affect the toning of an application in which it is used. In general, when the thickness of the cured product is 2.0 mm, the cured product preferably shows a light transmittance at a visible light wavelength of 560 nm of 1% or higher, more preferably 2% or higher.

Further, as in the case of the above transparency, the X-ray contrast property of the cured product of the polymerizable composition can be determined according to an application in which it is used. Based on the sensitivity of an X-ray which is generally used in dentistry (measured in accordance with the X-ray contrast property test of 5.11 of JIS T6514-1993), the cured product generally shows an Al equivalent of 45% or higher, preferably 55 to 400%, more preferably 80 to 300% or higher, when the thickness of the cured product is 2.0 mm.

Next, a composite material for dental use and industrial use will be described. As for the transparency of a cured product of a composite material obtained by adding the powder of the cured product of the above polymerizable composition to the polymerizable compound, the cured product should have transparency of such a degree that does not affect the toning of an application in which it is used, as in the case of the cured product of the polymerizable composition. In general, when the thickness of the cured product of the composite material is 2.0 mm, the cured product preferably shows a light transmittance at a visible light wavelength of 560 nm of 1% or higher, more preferably 2% or higher.

The amount of the powder of the cured product of the polymerizable composition in the composite material is determined according to a required X-ray contrast property, viscosity, operability and the like and is preferably 1 to 80 parts by weight, more preferably 5 to 70 parts by weight, based on 100 parts by weight of the polymerizable compound in the composite material.

The powder of the cured product of the polymerizable composition of the present invention is added to the composite material for dental use so as to impart the operability of the composite material, the X-ray contrast property and transparency of the cured product of the composite material, gloss after polishing, and ease of removal of an excess cured product when used as an adhesive resin cement.

As the polymerizable compound in the composite material, the polymerizable compound (C) used in the above polymerizable composition is used.

In consideration of the operability of the composite material and the physical properties of the cured product thereof, an inorganic filler is preferably also added to the composite material. The shape of the inorganic filler may be spherical or amorphous and is selected as appropriate together with the particle diameter. As for the type of the inorganic filler, there can be used known inorganic fillers such as the groups I, II, III and IV and transition metals of the periodic table and oxides, hydroxides, chlorides, sulfates, sulfites, carbonates, phosphates and silicates thereof, and mixtures and composite salts thereof. More specifically, the inorganic fillers include glass powders such as silicon dioxide, strontium glass, lanthanum glass and barium glass, quartz powder, barium sulfate, aluminum oxide, titanium oxide, barium salts, glass beads, glass fibers, bariumfluoride, lead salts, talc-containing glass powder, colloidal silica, silica gel, zirconium oxide, tin oxide, carbon fibers, and other ceramic powders. Although the inorganic filler may be used as it is, it is preferably rendered hydrophobic for the purpose of, for example, increasing the amount of the inorganic filler by increasing affinity between the polymerizable compound and the inorganic filler by use of a surface modifier. As the surface modifier, those described above can be used without limitations, and γ-(meth)acryloxypropyl dimethyl methoxysilane, γ-(meth)acryloxypropyl methyl dimethoxysilane, γ-(meth)acryloxypropyl trimethoxysilane, γ-(meth)acryloxypropyl dimethyl ethoxysilane, γ-(meth)acryloxypropyl methyl diethoxysilane and γ-(meth)acryloxypropyl triethoxysilane are particularly preferably used. As a surface modifying method, a method (dry method) comprising mixing a surface modifier or a surface modifier diluted with an organic-solvent-containing aqueous solution in which an organic solvent and water are uniformly mixed such as an ethanol aqueous solution with an inorganic filler by a ball mill, V-blender or Henschel mixer and then heat-treating the mixture at 50 to 150° C. for several minutes to several hours, a method (wet, slurry method) comprising adding an inorganic filler to an organic solvent such as ethanol, a solution in which an organic solvent and water are uniformly mixed such as an ethanol aqueous solution or water so as to form slurry, adding the above surface modifier, treating the resulting mixture at room temperature to a reflux temperature for several minutes to several hours, removing the solvent by a known method such as decantation or evaporation and then heat-treating the resulting product at 50 to 150° C. for several hours, and a method (spraying method) comprising spraying a surface modifier or the above aqueous solution directly on a high-temperature inorganic filler can be used. The inorganic filler should be treated as appropriate by a method taking the characteristics of a silane coupling agent and the inorganic filler into account. As a matter of course, a commercial inorganic filler having already been surface-modified may be used as it is or may be further surface-modified by the above methods or other methods. The above ethanol aqueous solution may be neutral or acidic. The amount of the surface modifier is preferably 0.1 to 20 parts by weight, more preferably 0.1 to 15 parts by weight, particularly preferably 0.1 to 10 parts by weight, based on 100 parts by weight of the inorganic filler.

Further, the average particle diameter of the inorganic filler is preferably 0.01 to 5 μm, more preferably 0.01 to 3 μm, much more preferably 0.01 to 1 μm, particularly preferably 0.01 to 0.1 μm, to impart gloss and transparency to a cured surface. To exhibit the above advantage, silica called a hydrophobic aerosil (Nippon Aerosil Co., Ltd.) such as R972, R972V, R972CF, RX200, RY200, R202, R805, R976, R812 or R812S or a hydrophilic aerosil such as OX-50 or 50 can be preferably used. Since they are commercially available as hydrophobed products of high-purity silicon dioxide aerosol, they are free from need to be surface-treated, and since the average particle diameter is 0.05 μm or smaller, i.e., the primary particle diameter is smaller than the wavelength of visible light, a cured product containing such silica hardly allows visible light to reflect diffusely and shows good transparency. Accordingly, these inorganic fillers can be preferably used. Of these, R972, R812, R812S and R805 are suitable.

Further, to impart mechanical strength and adjust viscosity, a filler having an average particle diameter of 5 to 100 μm, preferably 5 to 30 μm, may also be added in such an amount that does not impair the characteristics of the present invention.

The amount of the inorganic filler is selected in consideration of the shape and particle diameter of the inorganic filler, the viscosity of the composite material and other factors and is preferably 10 to 900 parts by weight, more preferably 10 to 600 parts by weight, much more preferably 10 to 400 parts by weight, based on 100 parts by weight of the polymerizable compound (C).

Further, as in the case of the above transparency, the X-ray contrast property of the cured product of the composite material can be determined according to an application in which it is used. Based on the sensitivity of an X-ray which is generally used in dentistry, the cured product generally shows an Al equivalent of 45% or higher, preferably 55 to 400%, more preferably 80 to 300%, when the thickness of the cured product of the composite material is 2.0 mm.

Applications of the polymerizable composition of the present invention, the cured product thereof and the composite material containing powder of the cured product are not particularly limited. Illustrative examples of dental applications include dental composite materials such as a sealant, a cavity lining material, adhesive resin cement, a resin filler (composite resin), a hard resin, and artificial teeth. Meanwhile, illustrative examples of industrial applications other than dental applications include industrial composite materials such as hard coat materials, binders for resins, glass plates for the windows of houses and vehicles in which inorganic glass has conventionally been used, shielding materials required to be ultraviolet-resistant or radiation-resistant, and degradation preventing materials for resins and the like.

Hereinafter, the present invention will be further described by use of Examples and Comparative Examples. The present invention shall not be limited by these Examples. The light transmittance (%) in Examples was measured by measuring a cured product having a thickness of 2.0 mm by use of a spectrophotometer (UV-160A, product of Shimadzu Corporation) at a visible light wavelength of 560 nm. To measure the X-ray contrast property (in accordance with the method described in 5.11 of JIS T6514-1993), a circular cured product having a thickness of 2.0 mm was X-ray photographed by X-ray control equipment (PCX-100, product of Asahi Roentgen Ind. Co., Ltd.) and then an Al equivalent (%) was calculated on the basis of the density (100%) of an image of an Al plate having the same thickness by a densitometer (PDA15, product of Konica Minolta Holdings, Inc.). The compressive strength was measured by immersing a cylindrical cured product with a diameter of 3 mm and a thickness of 3 mm which had been irradiated with light by visible light irradiation equipment (α-Light, product of Morita Corporation) for 3 minutes, in water (37° C.) for 24 hours and then measuring the resulting cured product by use of an autograph (AGS-2000G, product of Shimadzu Corporation) at a crosshead speed of 2.0 mm/min.

EXAMPLE 1

100 parts by weight of water-dispersed zirconia sol (product of CHEMAT CO., LTD., zirconia: 20 wt %, acetic acid: 15 wt %, water: 65 wt %, zirconia particle diameter: 5 to 10 nm), 400 parts by weight of methanol (hereinafter abbreviated as "MeOH") and 20 parts by weight of γ-methacryloxypropyl trimethoxysilane (hereinafter abbreviated as "γ-MPTS") were charged into an eggplant-shaped flask and stirred at room temperature for 48 hours. Then, 45 parts by weight of trimethylolpropane trimethacrylate (hereinafter abbreviated as "TMPT") was added and stirred for several minutes, and the solvent was then removed for an amount of 250 parts by weight by a rotary evaporator under reduced pressure at 40° C. Isopropyl alcohol (hereinafter abbreviated as "IPA") was added in the same amount as that of the removed solvent, and the resulting mixture was concentrated by a rotary evaporator under reduced pressure at 60° C. until most of the solvent was removed. Then, the resulting product was dried under reduced pressure by a dryer at a temperature of 80° C. for 6 hours to replace the solvent by TMPT which was a polymerizable compound so as to obtain 85 parts by weight of transparent polymerizable composition (zirconia concentration: 20 wt %).

To 100 parts by weight of the polymerizable composition, 0.3 parts by weight of benzoyl peroxide (hereinafter abbreviated as "BPO") was added as a polymerization initiator. After the resulting mixture was filled in a mold having a thickness of 2.0 mm, heat polymerization was carried out in a heating compression molding machine at a pressure of 0.5 MPa and 120° C. for 10 minutes. The obtained cured product of the transparent composite composition was evaluated with respect to light transmittance (%) at a visible light wavelength of 560 nm and an X-ray contrast property in terms of Al equivalent (%) (Table 1).

EXAMPLE 2

A polymerizable composition (zirconia concentration: 26 wt %) was prepared in the same manner as in Example 1 except that the amount of TMPT was changed to 22 parts by weight, and the light transmittance and X-ray contrast property of the cured product thereof were evaluated (Table 1).

EXAMPLE 3

A polymerizable composition (zirconia concentration: 30 wt %) was prepared in the same manner as in Example 1 except that the amount of TMPT was changed to 11.5 parts by weight, and the light transmittance and X-ray contrast property of the cured product thereof were evaluated (Table 1).

EXAMPLE 4

A polymerizable composition (zirconia concentration: 30 wt %) was prepared in the same manner as in Example 3 except that the polymerizable compound was a uniform mixture comprising ditrimethylolpropane tetramethacrylate (hereinafter abbreviated as "D-TMP") represented by the above formula (IV) and HX-220 (product of Nippon Kayaku Co., Ltd.) which was a polyester acrylate based compound represented by the above formula (V) in a molar ratio of D-TMP/HX-220 of ½, and the light transmittance and X-ray contrast property of the cured product thereof were evaluated (Table 1).

EXAMPLE 5

To a separable flask, 100 parts by weight of MeOH-dispersed titania sol (product of CATALYSTS & CHEMICALS IND. CO., LTD., titania coated with silica-zirconia: 30 wt %, MeOH: 70 wt %, titania particle diameter: 8 to 11 nm) and 100 parts by weight of MeOH were added and stirred for several minutes until a uniform mixture was obtained. To the mixture, 121.8 parts by weight of uniform hydrolyzed solution prepared by adding 76 parts by weight of γ-methacryloxypropylmethyl dimethoxysilane to 46 parts by weight of 0.1 wt % acetic-acid aqueous solution and stirring the mixture at room temperature for 1 hour for hydrolysis was added, and the resulting mixture was stirred in an oil bath of 90° C. for several minutes. Then, as 100 parts by weight of MeOH was gradually removed, 14 parts by weight of TMPT was added dropwise. After the resulting mixture was cooled to room temperature, 400 parts by weight of IPA was added, the solvent was removed by a rotary evaporator under reduced pressure at 40° C., the resulting product was dried under reduced pressure by a dryer at a temperature of 80° C. for 6 hours to completely replace the solvent with TMPT so as to obtain 120 parts by weight of transparent polymerizable composition (titania concentration: 25 wt %).

To 120 parts by weight of the polymerizable composition, 0.3 parts by weight of BPO was added as a polymerization initiator, and the cured product of the composite composition was obtained in the same manner as in Example 1. The light transmittance and X-ray contrast property of the obtained transparent cured product were evaluated (Table 1).

EXAMPLE 6

A polymerizable composition (titania concentration: 35 wt %) was prepared in the same manner as in Example 5 except that 26 parts by weight of 0.1 wt % acetic acid aqueous solution, 43 parts by weight of γ-methacryloxypropylmethyl dimethoxysilane and 13 parts by weight of TMPT were used, and the light transmittance and X-ray contrast property of the cured product thereof were evaluated (Table 1).

EXAMPLE 7

A polymerizable composition (titania concentration: 38 wt %) was prepared in the same manner as in Example 5 except that 26 parts by weight of 0.1 wt % acetic acid aqueous solution, 43 parts by weight of γ-methacryloxypropylmethyl dimethoxysilane and 6 parts by weight of TMPT were used, and the light transmittance and X-ray contrast property of the cured product thereof were evaluated (Table 1).

COMPARATIVE EXAMPLE 1

100 parts by weight of zirconia powder (prototype of Nippon Aerosil Co., Ltd.) having a primary particle diameter of 20 nm was added to a mixed solvent comprising 1,000 parts by weight of ethanol (hereafter abbreviated as "EtOH"), 5 parts by weight of γ-MPTS and 1 part by weight of distilled water and refluxed for 2 hours. Then, EtOH was removed by a rotary evaporator, and the resulting product was then dried under reduced pressure by a dryer at 80° C. in a nitrogen atmosphere for 10 hours. After 30 parts by weight of the modified zirconia powder was added to 100 parts by weight of TMPT and 0.3 parts by weight of BPO was added, a cured product was prepared in the same manner as in Example 1. It was a white cured product without transparency. The light transmittance and X-ray contrast property of the cured product were evaluated (Table 1).

COMPARATIVE EXAMPLE 2

100 parts by weight of water-dispersed zirconia sol (zirconia: 20 wt %, acetic acid: 15 wt %, distilled water: 65 wt %, zirconia particle diameter: 5 to 10 nm) and 400 parts by weight of MeOH were charged into an eggplant-shaped flask and stirred at room temperature for 48 hours. Then, 32 parts by weight of TMPT was added and stirred for several minutes, and the solvent was removed by a rotary evaporator under reduced pressure at 40° C. IPA was added in the same amount as 300 parts by weight of the removed solvent, and the resulting mixture was concentrated to completely replace the solvent by TMPT so as to obtain 67 parts by weight of white composite composition (zirconia concentration: 30 wt %) having no transparency.

To 67 parts by weight of the composite composition, 0.3 parts by weight of BPO was added as a polymerization initiator. After the resulting mixture was filled in a mold having a thickness of 2.0 mm, heat polymerization was carried out in a heating compression molding machine at a pressure of 0.5 MPa and 120° C. for 10 minutes. The light transmittance and X-ray contrast property of the obtained white cured product were evaluated (Table 1).

EXAMPLE 8

A polymerizable composition (titania concentration: 25 wt %) was prepared in the same manner as in Example 5 except that the polymerizable compound was a uniform mixture comprising 75 wt % of di(methacryloxyethyl)trimethylhexamethylene diurethane (hereinafter abbreviated as "UDMA") and 25 wt % of triethylene glycol dimethacrylate (hereinafter abbreviated as "3G"). The light transmittance and X-ray contrast property of the cured product thereof were evaluated (Table 1). Further, compressive strength was also measured and found to be 440 MPa.

COMPARATIVE EXAMPLE 3

To 100 parts by weight of polymerizable compound obtained by mixing 75 wt % of UDMA and 25 wt % of 3G, 0.3 parts by weight of camphorquinone, 0.06 parts by weight of 2-n-butoxyethyl p-N,N-dimethylaminobenzoate and 0.084 parts by weight of 2,6-di-t-butyl-p-cresol were added to prepare a photopolymerizable compound. After 25 parts by weight of titania powder (T-805, product of Nippon Aerosil Co., Ltd.) having a primary particle diameter of 21 nm was added to 100 parts by weight of the photopolymerizable compound, the resulting mixture was irradiated with light by use of visible light irradiation equipment α-light (product of Morita Corporation) for 3 minutes to give a circular cured product having a thickness of 2.0 mm. It was a white cured product having no transparency. The light transmittance and X-ray contrast property of the cured product were evaluated (Table 1). Further, although preparation of a test piece for measurement of compressive strength was attempted, the surface opposite to a surface exposed to light was not fully cured, thereby making it impossible to measure the compressive strength (it was not cured to 3.0 mm which was the thickness of the test piece).

TABLE 1

| Ex. No. | Solid Concentration (wt %) | Light Transmittance (%) | Al Equivalent (%) |
|---|---|---|---|
| Ex. 1 | 20 | 73.4 | 161 |
| Ex. 2 | 26 | 66.2 | 223 |
| Ex. 3 | 30 | 71.0 | 264 |
| Ex. 4 | 30 | 70.5 | 280 |
| Ex. 5 | 25 | 18.7 | 61 |
| Ex. 6 | 35 | 17.8 | 72 |
| Ex. 7 | 38 | 13.6 | 86 |
| Ex. 8 | 25 | 37.6 | 56 |
| C. Ex. 1 | 30 | 0.3 | 211 |
| C. Ex. 2 | 30 | 0.3 | 256 |
| C. Ex. 3 | 25 | 0.3 | 46 |

Ex.: Example,
C. Ex.: Comparative Example

EXAMPLE 9

A pass product obtained by milling the cured product obtained in Example 3 by a ball mill and sieving the resulting powder by a sieve having an opening of 53 μm was collected. After the product was washed with distilled water and EtOH, it was dried under reduced pressure by a dryer at a temperature of 80° C. for 2 hours (average particle diameter: 29 μm, hereinafter abbreviated as "T/Zr-1"). Then, to 100 parts by weight of polymerizable compound obtained by uniformly mixing 15 wt % of 3G, 25 wt % of 1,3-bis(methacryloxyethoxy)benzene (hereinafter abbreviated as "RDMA") and 60 wt % of 2,2-bis[4-(methacryloxyethoxy)phenyl]propane (hereinafter abbreviated as "2.6E"), 0.3 parts by weight of camphorquinone, 0.06 parts by weight of 2-n-butoxyethyl p-N,N-dimethylaminobenzoate and 0.084 parts by weight of 2,6-di-t-butyl-p-cresol were added to prepare a photopolymerizable compound.

To 100 parts by weight of the photopolymerizable compound, 42 parts by weight of T/Zr-1 and 18 parts by weight of R972 (product of Nippon Aerosil Co., Ltd.) which was hydrophobic colloidal silica were added to obtain a photopolymerizable compound. This was irradiated with light by use of visible light irradiation equipment α-light (product of Morita Corporation) for 3 minutes to obtain a transparent cured product of the composite material. The light transmittance, X-ray contrast property and compressive strength of the cured product were evaluated (Table 2).

EXAMPLE 10

A pass product obtained by milling the cured product obtained in Example 4 by a ball mill and sieving the resulting powder by a sieve having an opening of 53 μm was collected. After the product was washed with distilled water and EtOH, it was dried under reduced pressure by a dryer at a temperature of 80° C. for 2 hours (average particle diameter: 26 μm, hereinafter abbreviated as "D/Zr-2"). Then, to 100 parts by weight of the same photopolymerizable compound as used in Example 9, 42 parts by weight of D/Zr-2 and 18 parts by weight of R972 were added, and a transparent cured product of the composite material was obtained in the same manner as in Example 9. The light transmittance, X-ray contrast property and compressive strength of the cured product were evaluated (Table 2).

COMPARATIVE EXAMPLE 4

A pass product obtained by milling the cured product obtained in Comparative Example 1 by a ball mill and sieving the resulting powder by a sieve having an opening of 53 μm was collected (average particle diameter: 27 μm, hereinafter abbreviated as "Zr-3"). Then, to 100 parts by weight of the same photopolymerizable compound as used in Example 9, 42 parts by weight of Zr-3 and 18 parts by weight of R972 were added, and a cured product was prepared in the same manner as in Example 9. The cured product had no transparency. The light transmittance, X-ray contrast property and compressive strength of the cured product were evaluated (Table 2).

COMPARATIVE EXAMPLE 5

A pass product obtained by milling the cured product obtained in Comparative Example 2 by a ball mill and sieving the resulting powder by a sieve having an opening of 53 μm was collected (average particle diameter: 28 μm, hereinafter abbreviated as "Zr-4"). Then, to 100 parts by weight of the same photopolymerizable compound as used in Example 9, 42 parts by weight of Zr-4 and 18 parts by weight of R972 were added, and a cured product was prepared in the same manner as in Example 9. The cured product had no transparency. The light transmittance, X-ray contrast property and compressive strength of the cured product were evaluated (Table 2).

COMPARATIVE EXAMPLE 6

44.4 parts by weight of R972 and 0.5 parts by weight of BPO were added to 100 parts by weight of polymerizable compound comprising 90 wt % of TMPT and 10 wt % of UDMA, and heat polymerization was carried out by a heating compression molding machine at a pressure of 0.5 MPa and 120° C. for 10 minutes. A pass product obtained by milling the obtained cured product by a ball mill and sieving the resulting powder by a sieve having an opening of 53 μm was collected (average particle diameter: 23 μm, hereinafter abbreviated as "T-90f"). Then, to 100 parts by weight of the same photopolymerizable compound as used in Example 9, 42 parts by weight of T-90f and 18 parts by weight of R972 were added, and a cured product was prepared in the same manner as in Example 9. The light transmittance, X-ray contrast property and compressive strength of the cured product were evaluated (Table 2).

TABLE 2

| Ex. No. | Light Transmittance (%) | Al Equivalent (%) | Compressive Strength (MPa) |
| --- | --- | --- | --- |
| Ex. 9 | 4.0 | 128 | 434 |
| Ex. 10 | 4.5 | 135 | 485 |
| C. Ex. 4 | 0.3 | 99 | — |
| C. Ex. 5 | 0.3 | 112 | — |
| C. Ex. 6 | 1.0 | 38 | 323 |

Ex.: Example,
C. Ex.: Comparative Example

EXAMPLE 11

58.2 wt % of T/Zr-1 obtained in Example 9, 40 wt % of surface-treated GM8235 and 1.8 wt % of sodium salt of N-phenyl glycine were mixed together by a ball mill to form uniform powdery material.

39 wt % of 2-hydroxyethyl methacrylate, 15 wt % of epoxy resin (VR-90, product of Showa Polymer Co., Ltd.), 15 wt % of 2.6E, 10 wt % of 3G, 16 wt % of 4-methacryloxytrimellitic anhydride, 4 wt % of 4-methacryloxytrimellitic acid, 1 wt % of benzoylperoxide, 0.06 wt % of 2,6-di-t-butylresorcin and 0.03 wt % of 4-methoxyphenol were mixed together to form a uniform monomer mixture.

After the powdery material and the monomer mixture were placed in a mortar in the same amount and kneaded uniformly, the mixture was immediately filled in the same mold for measurements of light transmittance and an X-ray contrast property as used in Example 9.

The obtained cured product showed a light transmittance at a visible light wavelength of 560 nm of 50% and an X-ray contrast property in terms of Al equivalent of 150%. Thus, it had suitable properties as a dental cement material having transparency and an excellent X-ray contrast property.

The surface-treated GM8235 was prepared in the following manner.

316 ml of ethanol, 100 g of γ-methacryloxypropyl trimethoxysilane and 20 g of purified water were added to a separable flask at room temperature to prepare a uniform solution. While this solution was agitated, 1 kg of barium glass (average particle diameter: 1 am, product of Shot Co., Ltd., GM8235) was gradually added to prepare slurry. Then, after this slurry was refluxed under heating for 2 hours, the solvent was removed by an evaporator. The obtained powder was heated in a nitrogen atmosphere at 80° C. for 48 hours to obtain surface-treated GM8235.

EXAMPLE 12

100 parts by weight of the same water-dispersed zirconia sol as used in Example 1, 400 parts by weight of MeOH and 20 parts by weight of Y-MPTS were charged into an eggplant-shaped flask and stirred at room temperature for 48 hours. Then, after 11.5 parts by weight of TMPT was added and stirred for several minutes, the solvent was removed for an amount of 250 parts by weight by a rotary evaporator under reduced pressure at 40° C. To the content of the flask, a solution prepared by dissolving 0.3 parts by weight of BPO in 250 parts by weight of IPA was added. After concentrated again by a rotary evaporator until most of the solvent was removed, the content of the flask was transferred onto a tray and dried under reduced pressure at a temperature of 60° C. for 6 hours to replace the solvent by TMPT which was a polymerizable compound so as to obtain 52 parts by weight of transparent polymerizable composition (zirconia concentration: 30 wt %).

After this polymerizable composition was filled in a mold having a thickness of 2.0 mm, heat polymerization was carried out by a heating compression molding machine at a pressure of 0.5 MPa and 120° C. for 20 minutes. As a result, the obtained transparent cured product of the composite composition showed a light transmittance at a visible light wavelength (560 nm) of 71.4% and an X-ray contrast property in terms of Al equivalent of 281%.

EXAMPLE 13

A pass product obtained by milling the cured product obtained in Example 12 by a ball mill and sieving the resulting powder by a sieve having an opening of 53 μm was collected. After the product was washed with distilled water and EtOH, it was dried under reduced pressure at a temperature of 80° C. for 2 hours (average particle diameter: 25 μm, hereinafter abbreviated as "D/Zr-3"). Then, to 100 parts by weight of the same photopolymerizable compound as used in Example 9, 42 parts by weight of D/Zr-3 and 18 parts by weight of R972 were added, and a transparent cured product of the composite material was obtained in the same manner as in Example 9. As a result, the cured product showed a light transmittance of 4.3%, an X-ray contrast property in terms of Al equivalent of 133% and a compressive strength of 453 MPa.

EFFECT OF INVENTION

According to the present invention, there are obtained a polymerizable composition having excellent transparency and an X-ray contrast property, a cured product obtained by polymerizing the composition, and a composite material comprising powder of the cured product. They can be applied to a wider range of dental materials as well as to a wide range of industrial applications other than dental materials.

The invention claimed is:

1. A powder of a cured product of a polymerizable composition comprising:
   (A) an inorganic oxide having an X-ray contrast property and an average particle diameter of 100 nm or smaller, said inorganic oxide being that of at least one element selected from the group consisting of Ti, Zr and lanthanide,
   (B) a surface modifier comprising an alkoxysilane, said alkoxysilane being selected from the group consisting of γ-methacryloxypropyl methyl dimethoxysilane and γ-methacryloxypropyl trimethoxysilane and the amount of said surface modifier being 100 to 500 parts by weight based on 100 parts by weight of the inorganic oxide (A),
   (C) a polymerizable compound, said inorganic oxide being uniformly dispersed in the polymerizable compound (C), and
   (D) a polymerization initiator, whose cured product having a thickness of 2.0 mm shows a light transmittance at a visible light wavelength of 560 nm of 1% or higher and an X-ray contrast property in terms of Al equivalent of 45% or higher;
and said powder having an average particle diameter of 1 to 100 μm.

2. A composite material comprising the powder of claim 1.

3. A composite material comprising:
   a polymerizable compound,
   a polymerization initiator and
   the powder of claim 1.

4. A dental composite material comprising the powder of claim 1.

5. A dental composite material comprising:
a polymerizable compound,
a polymerization initiator and
the powder of claim 1.

6. The material of claim 5, whose cured product having a thickness of 2.0 mm shows a light transmittance at a visible light wavelength of 560 nm of 1% or higher and an X-ray contrast property in terms of Al equivalent of 45% or higher.

* * * * *